United States Patent [19]

Hauser

[11] Patent Number: 4,928,689
[45] Date of Patent: May 29, 1990

[54] RATE ADAPTIVE CARDIAC PACER SYSTEM HAVING LIVING CELL TISSUE FOR SENSING PHYSIOLOGIC DEMAND

[75] Inventor: Robert G. Hauser, Long Lake, Minn.

[73] Assignee: Cardiac Pacemakers, Inc., St. Paul, Minn.

[21] Appl. No.: 351,482

[22] Filed: May 15, 1989

[51] Int. Cl.⁵ ............................................. A61N 1/00
[52] U.S. Cl. ................................ 128/419 P; 128/786
[58] Field of Search ............ 128/786, 419 P, 783–785; 623/2

[56] References Cited

U.S. PATENT DOCUMENTS

| | | | |
|---|---|---|---|
| 3,514,791 | 6/1970 | Sparks | 623/2 |
| 4,280,514 | 7/1981 | MacGregor | 128/786 |
| 4,435,097 | 11/1984 | Bell | 424/95 |
| 4,534,366 | 8/1985 | Soukup | 128/786 |
| 4,553,272 | 11/1985 | Mears | 623/1 |
| 4,576,183 | 3/1986 | Plicchi et al. | 128/419 PG |
| 4,716,887 | 1/1988 | Koning et al. | 128/419 PG |
| 4,719,920 | 1/1988 | Alt et al. | 128/419 PG |
| 4,719,921 | 1/1988 | Chirife | 128/419 PG |
| 4,784,160 | 11/1988 | Szilagyi | 128/419 P |
| 4,784,161 | 11/1988 | Skalsky et al. | 128/419 P |

Primary Examiner—Francis Jaworski
Assistant Examiner—George Manuel
Attorney, Agent, or Firm—Haugen and Nikolai

[57] ABSTRACT

Described herein is a cardiac pacer pulse generator and lead combination in which sinus node cell tissue is harvested or cultured and appropriately affixed to the distal end of the pacing lead to generate electrical depolarization signals whose rate changes with blood-oxygen levels and hormonal activity. The lead includes a sensing electrode for picking up these depolarization signals and applying them to the rate adaptive pacemaker. The pacemaker then functions to produce heart tissue stimulating pulses at a rate dictated by the body's physiologic demand.

11 Claims, 1 Drawing Sheet

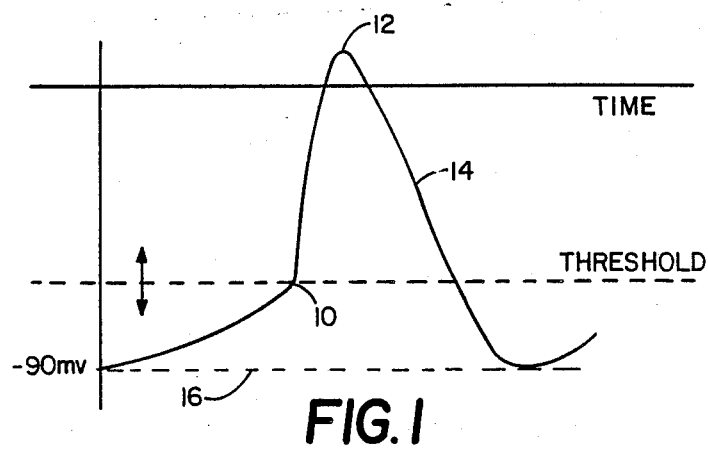
FIG. 1
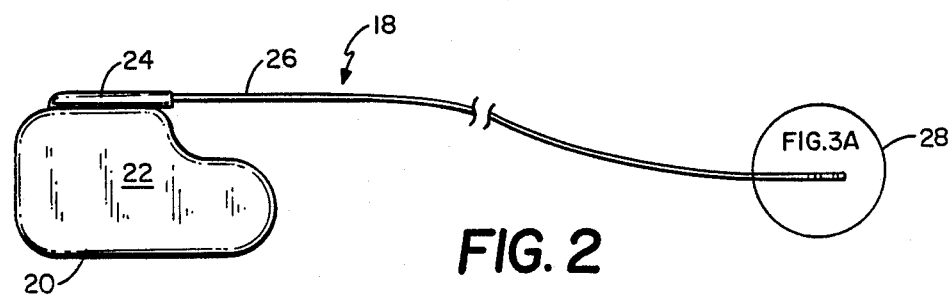
FIG. 2
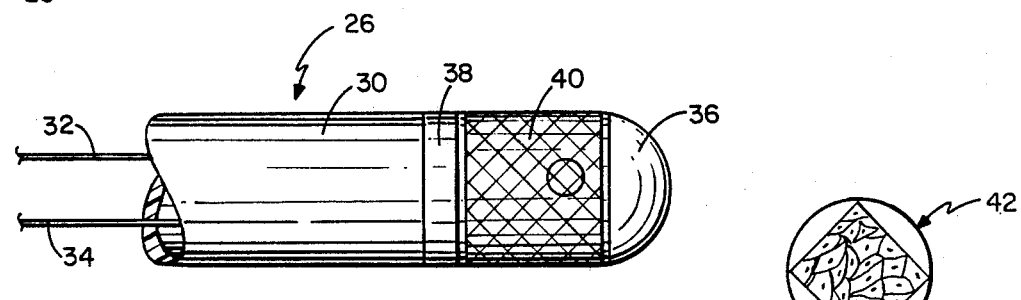
FIG. 3A
FIG. 3B
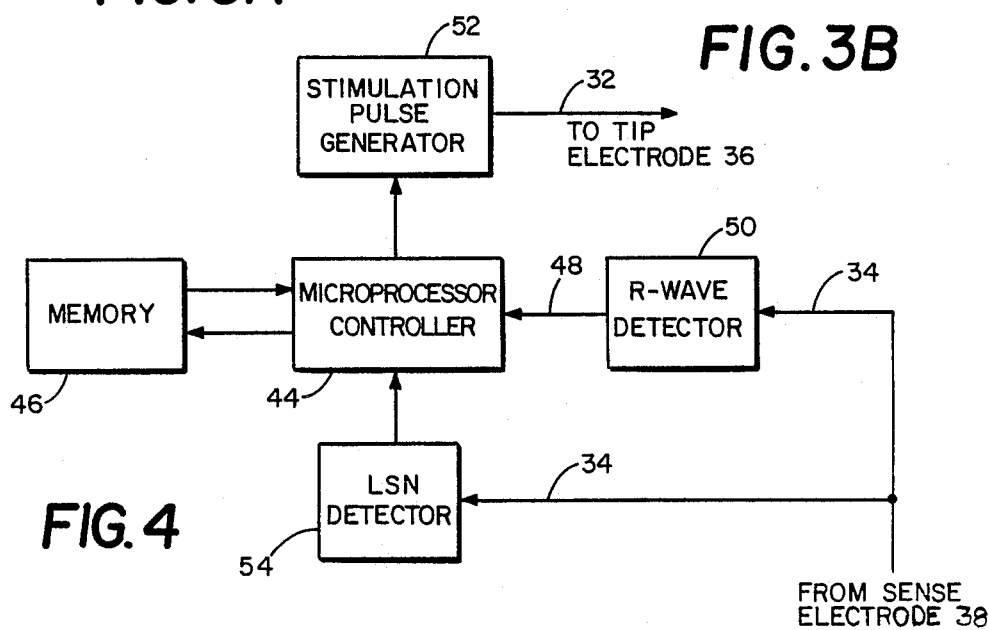
FIG. 4

RATE ADAPTIVE CARDIAC PACER SYSTEM HAVING LIVING CELL TISSUE FOR SENSING PHYSIOLOGIC DEMAND

BACKGROUND OF THE INVENTION

I. Field of the Invention

This invention relates generally to a cardiac pacing system in which the pacing rate is adjustable to meet physiologic demand and more particularly to a rate adaptive pacing system in which living cell tissue is used to sense metabolic need.

II. Discussion of the Prior Art

For approximately 25 years now, implantable cardiac pacers have been used to treat patients with defects in the cardiac conduction system, such as complete or partial heart block, bradycardia attributable to sick sinus node, atrial disease, A-V nodal disease, and even in cases of congestive heart failure. More recently, attempts have been made to more closely mimic normal heart operation. For example, attempts have been made to emulate the action of the S-A node and this has led to a class of cardiac pacers referred to as "rate adaptive pacers", "rate responsive" or sometimes "physiologic pacers". In these latter devices, some sort of a sensor is used to measure such things as blood temperature, blood oxygen saturation, body motion or activity, blood pH, respiratory rate, etc., and then use the sensed information to adjust the rate at which the pacer pulses are generated so as to accommodate the patient's level of activity.

In the introductory portion of the Koning et al Pat. No. 4,716,887, there is set forth a synopsis of several prior art patents relating to rate adaptive pacers and, especially, the particular physiologic parameters used heretofore for developing a rate control signal for an implanted pulse generator. Readers wishing additional background concerning the state of the prior art are referred to the Koning et al Patent and the references cited therein.

Most prior art pacemakers are prescribed for patients who have heart block and/or sinus node disease. Standard pacemakers pace either one chamber (atrium or ventricle), or both chambers (atrium and ventricle). Dual chamber pacemakers, commonly referred to as VDD and DDD pacemakers, are capable of tracking sinus node or atrial activity and then pacing the ventricle in synchrony. Such devices increase the pacing rate to meet the growing need for blood flow during periods of stress or exercise. Standard single chamber pacemakers, generally speaking, are not configured to adjust the pacing rate automatically, but rate responsive or rate adaptive pacemakers, both single and dual chamber, have been designed to be able to change pacing rate based on some direct or indirect indicator of stress or exercise. As set out in the Koning patent, various ones of these rate responsive pacemakers monitor a variety of conditions. None of them, however, truly mimics the sinus node which is the normal pacemaker or control center for the heart and the one true indicator of appropriate heart rate. The sinus node cells are responsive to both nerve impulses from the autonomic nervous system and to blood chemistry to set the heart rate. More particularly, the concentration of oxygen and carbon dioxide in the bloodstream as well as other chemical agents, such as drugs, hormones, etc., are integrated in the sinus node and affect the rate of depolarization/repolarization of the cells comprising that node.

Generally speaking, mechanical, electrical or chemical sensors all suffer from one or more serious disadvantages, typically that they lack physiologic sensitivity and specificity. As such, such auxiliary sensors tend to be either too slow or too fast and thus require additional prosthetic components. Unlike artificial sensors of the prior art, the present invention provides sensitive and specific responses to stress and exercise and does not rely on a purely prosthetic sensor which is oftentimes the weakest link in terms of reliability as well as adding complexity to the overall pacing system.

SUMMARY OF THE INVENTION

In accordance with the present invention, there is provided a living adaptive pacemaker (LAP) comprising living sinus node tissue, a pacing lead, and a pulse generator. The living sinus node (LSN) may be harvested or cultured tissue which possesses the properties of the sinus node. The LSN is located within a delivery vehicle attached to the tip of a pacemaker lead. The delivery vehicle contains the necessary environment, e.g. nutrients required to support the LSN during manufacture, shipment, storage and post-implant.

The pacing lead of the present invention, in addition to supporting the LSN delivery vehicle, also includes a pacing electrode for applying electrical stimulating signals to the heart. It carries a sensing electrode for detecting the depolarization of the LSN cells. The pacing lead and the associated pulse generator are specifically designed to allow monitoring of LSN electrical activity, to process that electrical activity and to respond with appropriately timed pacing stimuli, if required.

The LSN, therefore, can be considered as a transplanted sinus node configured to govern pacing rate of an implantable pacemaker in the same physiologic way as the normal sinus node would. In particular, it will react to autonomic tone and other factors that ordinarily effect sinus rate. Because the LSN alone, if grafted in place in the atrium or in the ventricle may be incapable of functioning completely as a normal sinus node by causing the atria to contract, the lead and pulse generator become important elements of the overall system comprising the present invention. A sensing electrode on the lead will detect the LSN's activity and trigger the pulse generator. The output from the pulse generator will then be delivered, via the lead, to the atria and/or ventricle. In this mode, then, the rate responsive pacer of the present invention uses the LSN only to govern pacing rate and not to itself pace the heart. The pacing pulse generator may be programmed to permit the LSN to directly pace the heart, with the pulse generator and lead serving as a back-up, or to interact with the LSN in one or both chambers.

OBJECTS

It is accordingly a principal object of the present invention to provide an improved rate responsive pacing system for treating cardiac disfunction.

Another object of the invention is to provide a rate adaptive pacing system in which the sensor of physiologic demand comprises living cell tissue reactive to blood-gas concentrations, chemical agents and nerve impulses from the autonomic nervous system.

Yet another object of the invention is to provide a rate responsive cardiac pacing system in which harvested or cultured sinus node cells are incorporated into the pacing lead as a sensor for physiologic demand.

A still further object of the invention is to provide a pacing system comprising a variable rate pulse generator and a lead coupled thereto where the lead includes a stimulating electrode, a substrate supporting living cell tissue and a sensing electrode whereby depolarization signals produced by the lead-supported tissue provides, via the sensing electrode, an input to the variable rate pulse generator for adjusting its rate in accordance with metabolic need.

Still other more specific features and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE DRAWINGS

FIG. 1 illustrates the manner in which the membrane potential of S-A node cells varies with time;

FIG. 2 is a generalized diagram of the living adaptive pacer of the present invention;

FIG. 3 is an enlarged partial view of the distal end portion of the pacing lead used in the system of FIG. 2; and FIG. 4 is a block diagram of the pacing pulse generator portion of the system of FIG. 2.

DESCRIPTION OF THE PREFERRED EMBODIMENT

The sino-atrial (S-A) node comprises a small collection of cells disposed within the upper wall of the right atrium. These cells have a property which distinguishes them from other cardiac cell tissue in that they permit a constant, slow leakage of sodium ions through the cell membrane. With other types of cells, however, the cell membrane ordinarily excludes sodium. Referring to Figure 1, the waveform of the membrane potential is illustrated for S-A node cells. It will be observed that when the cells have depolarized, the membrane potential falls to approximately $-90$ mv and that as positive sodium ions slowly invade the cell, the membrane potential slowly rises until a threshold level is reached (numeral 10) at which time the cell depolarizes and rises rapidly to a positive potential of approximately 20 mv (numeral 12). At this time, the S-A node cells begin to pump out the sodium, thereby repolarizing over the interval spanned by the descending segment 14 to the "resting potential" 16 where the cycle begins anew. Since the cells will be clustered, the resulting signal to be sensed by the pulse generator will be a summation of the individual depolarization.

The S-A node cells are highly sensitive to changes in oxygen concentration in the blood, to circulating hormones, to certain drugs as well as to impulses coming from the nervous system. The rate at which the node cells fire (depolarize) depends upon the above factors, increasing when the body needs more oxygen or is under stress, and decreasing when at rest.

In a healthy heart, the depolarization of the S-A node travels as a wave across the muscle tissue comprising the atrium. Upon reaching another specialized collection of cells, namely the A-V node, it is made to fire and sends a delayed response through the Bundle of His and through the right and left bundle branches and through all Purkinge fibers to cause a coordinated contraction of the ventricular myocardium.

Where because of disease or other reasons, a block exists in the conduction path of the heart or in the case of rhythm disturbances resulting from congenital disorders or otherwise, the conduction paths of the heart are blocked, the patient would be a good candidate for an implantable pacemaker of the type described herein and which is illustrated generally in FIG. 2 of the drawings. The pacing system is indicated generally by numeral 18 and includes an implantable pacemaker 20 contained within a body-compatible, hermetically sealed container 22. The electrical circuitry housed within the container 22 has input and output connections contained within a header block 24 into which is fitted the terminal connector (not shown) of a pacing lead 26. The pacemaker can 22 may be implanted at any one of a number of locations within the body in accordance with known techniques and the lead 26 is routed through the vascular system and into the heart.

Referring next to FIG. 3, there is shown an enlarged view of the distal end portion of the lead assembly 26 which, in FIG. 2, is shown as being enclosed within the circle 28. The lead 26 is seen to comprise an elongated tubular sheath 30 which is preferably fabricated from a suitable, body-compatible, flexible plastic, such as Silastic, polyurethane or any of the other plastic materials commonly used in the fabrication of conventional pacing leads. The tubular sheath 30 is seen to surround first and second conductors 32 and 34 which join to the proximal connector of the lead (not shown). The conductor 32 also connects internally to a distal tip electrode 36 which functions as the stimulating electrode. Conductor 34 connects internally to a surface ring electrode 38 which functions as a sensing electrode.

Inserted in the lead body between the tip electrode 36 and the sensing electrode 38 is a porous substrate 40 used for in-vitro culture of mammalian anchorage-dependent cells. In one arrangement, the substrate may comprise mitogenic calcium compounds which are non-toxic to cells. The porous calcium substrate is preferably ring-shaped and will have an irregular or textured surface to increase the surface area available for cell growth. A particular solid substrate suitable for use in the present invention comprises porous hydroxyapatite or tricalcium phosphate forms of calcium phosphate made by compacting granules of such compounds, and non-porous granules or solid bodies of calcium carbonate. Such substrates have been found to support cell growth in layers many cells thick rather than the monolayer cell growth exhibited by in-vitro cell culture using different substrates. Moreover, it has been found that cells grown in the calcium substrate using an appropriate nutrient growth solution maintain their phenotype, meaning that the cultured cells exhibit the same types of characteristics as the natural cells. The substrate 40, being porous, becomes ingrown with the sinus node cells as indicated by the enlargement of one small area of the substrate 40 and identified by numeral 42.

Referring next to FIG. 4, there is shown by means of a block diagram the circuitry comprising the pacing electronics contained within the housing 22. It is preferably a microprocessor controlled device including a microprocessor controller 44 having associated therewith a memory 46 for storing various programmable parameters, such as stimulating pulse width, escape interval, sensitivity, etc. When operating in a demand mode, the microprocessor controller 44 is configured to receive input signals on line 48 from a R-wave detector circuit 50. The input to the R-wave detector circuit comes from the sense electrode 38, via conductor 34, in the lead 26. In the event that the escape interval elapses before a natural R-wave signal is detected, the microprocessor controller 44 triggers the stimulation pulse generator 52 to issue a stimulating pulse. This pulse is delivered through the lead 26 on conductor 32 to the tip electrode 36 which, typically, will be positioned at the apex of the right ventricle.

The sinus node cell tissue on the substrate 40 is immersed in the bloodstream and, as such, responds to changes in blood oxygen concentration, catecholamines and other hormones to effectively shift the threshold voltage 10 at which cell depolarization takes place. The lead-mounted cell depolarization signal is picked up by the sensing electrode 38 and fed back over lead 34 to the LSN detector circuit 54 which amplifies and shapes the pulse applied to the microprocessor controller 44. The microprocessor controller is programmed to compute the time interval between successive LSN depolarization signals to, in turn, adjust the escape interval of the demand pacing circuitry. This, in turn, adjusts the rate at which stimulation pulse generator 52 provides ventricular stimulating pulses to the tip electrode 36 when natural R-wave activity is lacking.

Persons skilled in the field of biochemistry can readily formulate a culture media for maintaining and growing S-A node cells or their equivalent and to devise additives which will reduce adverse immune reactions to the cell structures on the tip of lead 26. Similarly, the cells will reside in a mechanical structure or capsule that will allow the cells to remain viable and protected from mechanical stresses.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An implantable apparatus for pacing the heart in accordance with a sensed physiologic demand comprising:
   (a) adjustable rate demand pacer for implantation in a human body, including means for sensing naturally occurring ventricular depolarization signals originating within the heat tissue and coordinating the application of electrical stimulation signals to said heart tissue with said naturally occurring ventricular depolarization signals; and
   (b) a pacing lead for implantation in said human body, at least a portion of said lead being disposed within the heart, said lead being electrically coupled to said adjustable rate demand pacer and having a stimulating electrode, a sensing electrode and a substrate supporting living sinus, node, cell tissue, said sensing electrode detecting through said substrate depolarization of said sinus node cell tissue and delivering a rate control signal to said adjustable rate demand pacer for controlling the rate at which said electrical stimulation signals are delivered to said stimulating electrode.

2. The implantable apparatus as in claim 1 wherein said sinus node cell tissue responds to changes in hormonal activity and blood oxygen concentration in producing said depolarization of said sinus node cell tissue.

3. The apparatus as in claim 1 wherein said substrate is porous and wherein said sinus node cell tissue is cultured on said substrate.

4. The apparatus as in claim 1 wherein said sinus node cell tissue comprises an autologous graft.

5. The apparatus as in claim 1 wherein said sinus node cell tissue comprises an allogeneic graft.

6. The apparatus as in claim 1 wherein said porous substrate is permeable to a nutrient media for nourishing said sinus node cell tissue.

7. The apparatus as in claim 6 wherein said substrate is a calcium compound.

8. A rate adaptive cardiac pacing system comprising:
   (a) an implantable pulse generator for producing stimulating pulses at a rate related to the physiologic demand of the body in which said pulse generator is implanted;
   (b) lead means coupled to said pulse generator for applying said stimulating pulses to a heart in said body; and
   (c) sinus node cell tissue grown on said lead means and responsive to changes in blood chemistry for supplying rate control signals to said implantable pulse generator.

9. The pacing system as in claim 8 wherein said pulse generator comprises a demand-type cardiac pacer whose escape interval is altered by said rate control signals.

10. The pacing system as in claim 9 wherein said pulse generator is a dual chamber, demand-type cardiac pacer.

11. The pacing system as in claim 10 wherein said lead means comprises:
    (a) an elongated tubular member having a proximal end, a distal end portion and at least one lumen extending therebetween;
    (b) a stimulating electrode disposed on said tubular member at said distal end portion;
    (c) a sensing electrode disposed on said tubular member at said distal end portion;
    (d) substrate means on the surface of said tubular member proximate said sensing electrode, said substrate member supporting said sinus node cell tissue;
    (e) connector means at said proximal end of said tubular member for mating with said pulse generator; and
    (f) conductor means extending through said lumen joining said sensing electrode and said stimulating electrode to said connector means.

* * * * *